United States Patent
Herweck et al.

(10) Patent No.: US 6,565,594 B1
(45) Date of Patent: May 20, 2003

(54) TUNNELING DEVICE

(75) Inventors: Steve A. Herweck, Nashua; David P. Cross, Atkinson, both of NH (US)

(73) Assignee: Atrium Medical Corporation, Hudson, NH (US)

( * ) Notice: Subject to any disclaimer, the term of this patent is extended or adjusted under 35 U.S.C. 154(b) by 118 days.

(21) Appl. No.: 08/937,083

(22) Filed: Sep. 24, 1997

(51) Int. Cl.⁷ .................................................. A61F 2/06
(52) U.S. Cl. ...................................................... 623/1.11
(58) Field of Search ............................. 623/1.46, 13.11, 623/13.16, 1.11; 606/108

(56) References Cited

U.S. PATENT DOCUMENTS

| | | | |
|---|---|---|---|
| 2,836,181 A | 5/1958 | Tapp | 128/334 |
| 3,981,299 A | 9/1976 | Murray | 128/349 B |
| 4,574,806 A | 3/1986 | McCarthy | 128/334 R |
| 4,733,665 A | 3/1988 | Palmaz | 128/343 |
| 4,739,762 A | 4/1988 | Palmaz | 128/343 |
| 4,775,380 A * | 10/1988 | Seedhom et al. | 623/13.16 |
| 4,776,337 A | 10/1988 | Palmaz | 128/343 |
| 4,846,191 A | 7/1989 | Brockway et al. | 128/748 |
| 5,122,154 A | 6/1992 | Rhodes | 606/198 |
| 5,234,438 A | 8/1993 | Semrad | 606/108 |
| 5,246,452 A | 9/1993 | Sinnott | 623/1 |
| 5,269,755 A | 12/1993 | Bodicky | 604/53 |
| 5,306,240 A | 4/1994 | Berry | 604/51 |
| 5,370,610 A | 12/1994 | Reynolds | 604/43 |
| 5,393,302 A * | 2/1995 | Clark et al. | 623/13.11 |
| 5,443,499 A | 8/1995 | Schmitt | 623/1 |
| 5,474,824 A | 12/1995 | Martakos et al. | 428/36.9 |
| 5,607,443 A | 3/1997 | Kieturakis et al. | 606/192 |
| 5,804,318 A * | 9/1998 | Pinchuk et al. | 623/1.46 |

FOREIGN PATENT DOCUMENTS

| | | |
|---|---|---|
| EP | 0 515 007 A1 | 11/1992 |
| WO | WO 95/05131 | 2/1995 |
| WO | WO 95/05132 | 2/1995 |
| WO | WO 96/00103 | 1/1996 |
| WO | WO 96/28115 | 9/1996 |

OTHER PUBLICATIONS

Brochure: Atrium Hybrid PTFE, *Vascular Grafts Product Catalog*.
Brochure: IMPRA Kelly–Wick Access Tunneler Set KW2000.
Brochure: The Gore Tunneler.
Brochure: Scanlan Vascular Tunneler System.
IMPRA Technical Report (TR–106), *Angioaccess Tunneling*.
Brochure: Atrium Hybrid PTFE, *Vascular Grafts Product Catalog* (Code No. Cross Reference) 1995–96.
Brochure: Introducing the New Expanded PTFE: Diastat Vascular Access Graft (by Gore).

\* cited by examiner

*Primary Examiner*—David J. Isabella
(74) *Attorney, Agent, or Firm*—Lahive & Cockfield, LLP (57) ABSTRACT

A tunneling device, which is implantable in a body, includes a flexible covering to protect a medical from contamination during the handling and implantation of the device in the body. The tunneling device of the present invention may optionally include a rigid tunneler tip that allows for attachment of the tunneling device to a tunneler instrument prior to the implantation process.

15 Claims, 6 Drawing Sheets

TUNNELING DEVICE

FIELD OF THE INVENTION

This invention relates generally to tunneling devices which are implantable in a body, and more specifically to tunneling devices that include a flexible covering to protect the device from contamination during the handling and implantation of the device in the body. A tunneling device of the present invention may optionally include a tunneler tip that allows for attachment of the tunneling device to a tunneler instrument during the implantation process.

BACKGROUND OF THE INVENTION

It is commonly known that cardiac bypass surgery is a means to divert the flow of blood around arteries or veins that have become occluded or stenosed, and thus eliminate an impediment to the requirement of blood flow. A vascular graft which is a tubular device that is suitable for implantation in the body is used to reestablish or redirect the flow of blood beyond the blockage area. Surgical implantation procedures require placement of the vascular graft within the subcutaneous tissue. Vascular graft implantation requires the creation of an anatomic or subcutaneous pathway commonly called a graft tunnel. Tunneling is a required surgical step in the vascular bypass procedure for all peripheral, vascular access and extra anatomical graft locations which result in localized dissection injury to tissue. The tunnel diameter relative to the implant diameter, as well as the abrasive force exerted by the implant during insertion have a significant impact on the resultant trauma to this tissue and its healing response to both the blunt dissection of the tunnel space tissue and the vascular graft material.

It is advantageous in the clinical setting to minimize trauma to this tissue through the use of an improved tunneling technique and implant device. The conventional approach to creating a graft tunnel or space for the vascular graft is with the use of a rigid rod like device called a graft tunneler or tunneler instrument. Tunneler instruments come in varying sizes. They are usually very bulky, and require cleaning and sterilization before reuse. Improper size selection of the tunneler instrument or improper tunneling technique may result in a larger than required tunnel path through the tissue. An example of a tunneler instrument which has been designed to minimize the problem of over-sizing a tissue tunnel is the KELLY-WICK tunneling set from Bard® Impra®, which is specifically designed for the implantation of vascular grafts without a tunnel sheath. Hence, this instrument is a "sheathless" system that draws a vascular graft through the dissected tissue tunnel which is created by a insertion of a rigid, bullet tipped rod through a skin incision, and forced horizontally through the subcutaneous tissue.

These type of tunneler instruments are reusable but expensive, and consequently hospitals often maintain only a limited supply of these instruments for operating room use. Since these instruments are reusable, they must be cleaned, packaged and resterilized between use. Frequently in emergency vascular surgery situations, the proper sized tunneling tip, whether it be a specific diameter, length or size, is not readily available. Consequently, the surgeon is forced to use an improper sized bullet tip (not matched to the outside diameter of the implant), or use a make-shift device. This may result in the creation of a vascular graft tunnel that is too large or too small for the graft, causing unnecessary or increased patient complications. If the tunneler instrument used creates a tunnel track that is too large for the size vascular graft being implanted, the tubular graft will not fit snugly within the tunnel and large "tunnel spaces" will exit along the entire length of the graft. This event is considered to be a major contributor to postoperative graft complications such as wound inflammation, graft material infection, and or seroma formation about the outside space of implanted graft. With an improper or "over-sized" tunnel, a significant amount of blood may pool and collect around the entire length of the implant, causing postoperative graft failure due to poor healing of the localized tissue, graft infection, and painful tissue swelling due to fluid accumulation between the dissected tissue and the implant.

Using a tunneler instrument to create a tunnel for the insertion and implantation of the vascular graft, the rigid rod like device is forcefully passed through the subcutaneous tissue horizontally between two surgically prepared incisions, until the bullet tip end is exposed at the second incision or exit wound. Once this tunneler tip is exposed, the tubular vascular graft material is placed over the bullet tipped device and tied onto the end of the indwelling tunneler rod tip with a sterile suture thread. The surgeon must carefully tie the graft to the tunneler rod with several suture knots, so as to avoid the graft from slipping off of the tunneler tip when pulled beneath the skin and into the implant position. After the vascular graft has been pulled through the dissected tissue cavity into final position, the vascular graft is then cut free at the tied end of the tunneler rod. Since the graft is exposed to the operative wound during attachment and insertion of the graft, the sterility and purity of the graft material are compromised. The process of suturing the graft to the tunneler rod and the manipulation of the graft by the surgeon further compromise the sterility of the device as a result of this "hands on" contact. Handling of the graft material during a tunneling procedure by contact with the nurse's and surgeon's gloves also increases the risk of infection by contamination from glove contact and operative wound/skin surface contact.

Another source of tissue trauma and postoperative graft complications can be created by the graft material itself due to the way the surgeon ties the graft to the tunneler. If not carefully prepared by the surgeon, part of the graft material may freely protrude over the tunneler instrument rod, forming a lip of free graft material in front of the suture tie. When the graft is forcibly pulled into and through the dissected tissue tunnel, such pulling action causes this graft material to compress, bunch up and create an abrupt or raised area in front of the suture tie which bluntly plows through the tissue, increasing the diameter of the tunnel and effectively increasing the amount of device drag in an abrasive manner, further traumatizing tissue along the entire tunnel track. This plowing action not only increases the potential for even more undesirable bleeding and tunnel track inflammation, but makes more work for the surgeon during graft insertion, particularly during long peripheral and extra anatomical bypass. This forceful graft insertion technique and risk of patient complications occurs with all commercially available vascular grafts when used with "sheathless" tunneler instruments.

"Pre-wetting" of the vascular graft material is another undesirable complication that occurs with traditional sheathless tunnelers. Since vascular grafts are constructed from porous biomaterials designed to encourage rapid cell ingrowth following implantation, for example vascular grafts made from expanded polytetrafluoroethylene (PTFE), it is known that microporous graft materials should not be "pre-wetted" or "presoaked" with blood. These conditions lead to fluid leakage through the graft material once blood flow is restored within the implant, much the way a canvas tent would leak in a rain storm. If, during insertion of the graft with a traditional sheathless tunneler instrument, the tunneler tip is undersized in comparison to the outside diameter of the graft being implanted, the leading 2–5 cm length of graft material will become completely saturated with blood during the process of dragging the graft through the tissue. This is caused by the pressure placed on the tissue during graft insertion due to the initial under-sized tunnel tract. Since the thickness of the graft material adds to the outer diameter of the original bullet tip outer diameter, the leading edge of the graft material is forcibly dragged through the bleeding tissue. The pressure on the graft is controlled by the size of the tunneler tip which bluntly dissected the original tunnel space. The amount of pressure placed on the adjacent bleeding tissue and onto the graft material varies according to surgical technique and tunneler tip size selection, and thus the length and amount of graft material saturation with blood varies from patient to patient. This accounts for why some vascular graft patients unpredictably develop "seroma" formation, a serious complication of fluid accumulation around all or part of the graft material, causing moderate pain, edema and swelling of the closed wound, interstitial edema and inflammation, poor healing of the implant material, graft thrombosis and the most critical of all, systemic infection, which has an unacceptable morbidity rate. Therefore, use of a sheathless tunneler technique is not without its risk of patient complications following surgery. Such vascular graft complications may not appear for up to 30 days after patient discharge from the hospital. Hence, any surgical technique with a sheathless tunneler device which could reduce these unpredictable postoperative conditions would be clinically significant and cost effective in today's world of managed care medicine.

One example of a popular "sheathless" tunneler is the KELLY-WICK tunneling set commercially available from Bard-Impra, Tempe, Ariz. This tunneler is a one piece rod, specifically designed for the implantation of peripheral, vascular grafts (non aortic, non coronary), whereby it is the desire of the surgeon to minimize the outer tunnel space around the vascular graft implant. This tunneler is named after the two doctors that designed the device. The device is comprised of a rigid rod that is permanently connected to a knurled handle. The rod may vary in shape and size from a straight shaft to a semicircular shaft, allowing for a variety of surgical techniques and/or placement locations. The rod is fabricated from a rigid material such as stainless steel. The rod of the instrument may terminate with a threaded on bullet tip at the opposite end to the handle. The threaded rod and bullet tip facilitates the use of different size bullet tips with a single tunneler rod to create different size tissue channels or tunnels. The Kelly-Wick tunneler is manually forced through the tissue horizontally between two incisions by the surgeon to thereby create a bluntly dissected tunnel. When tunnel dissection is completed with the bullet tip end protruding out of the distal skin incision, the vascular graft to be implanted is then attached to the tunneler tip by pushing one end of the tubular graft over the bulbous end of the bullet tip, carefully suturing and tying the end of the graft material to the bullet tip with one or two sterile suture threads. Once tied to the tunneler instrument, the vascular graft is drawn into the subcutaneous tissue channel by pulling the tunneler rod out through the first skin incision until the graft is pulled completely into the patient. When appropriately positioned between the area being bypassed, the surgeon cleanly cuts the graft away from the sutured end of the tunneler rod and tip.

While the KELLY-WICK sheathless tunneler is a popular surgical device, it has all of the previously described disadvantages. This tunneler requires that the graft be surgically positioned by pulling the graft through bluntly dissected tissue, causing further abrasion due to surface friction between the outside surface of the graft and the tissue. Further, the graft is attached to the bullet tip by sliding the graft over the tip and tying the tip and graft together. The mating of the tip and graft in this fashion creates a square edged lip at the end of the graft which tends to compress and enlarge when the graft is pulled through the tunnel, creating a "plowing" effect and causing further abrasion to the tissue wall and a larger tunnel channel. Depending on the care and preparation of the suture tying technique by the surgeon, the tunnel cavity is sometimes enlarged so that the graft does not seat snugly in the tunnel and the extra space about the graft implant would likely fill with blood and interstitial fluid.

An alternative tunneling technique uses a two (2) part tunneler instrument called a rigid "sheath tunneler," which includes an oversized rigid metal or plastic hollow tube with a removable bullet shaped dissection tip on one end, and an internal smaller diameter indwelling rod for attaching the vascular graft material. The two part rigid sheath tunneler allows the surgeon to easily pull the vascular graft through the internal lumen of the rigid outer sheath, being substantially oversized in comparison to the outside diameter of the vascular graft. Once the graft has been pulled into the rigid sheath, the graft material is cut free from the "pull-through rod" and the subcutaneous rigid sheath is then extracted out from the tissue track and exit wound without extracting the graft. These rigid sheath tunnelers may at times be difficult to use since the rigid tubular sheaths are awkward to extract from the subcutaneous tissue due to the surface friction of the indwelling instrument. Sheath tunneler instruments require the surgeon to hold the graft in position with the pull-thru rod, a vascular clamp or gloved hands simultaneous to pulling on the rigid tubular sheath to remove it from the subcutaneous tissue.

An example of a "sheath" tunneler is the GORE tunneler which is produced by W. L. Gore and Associates, Inc. of Flagstaff, Ariz. This two part tunneler instrument is used to implant a vascular graft subcutaneously with an oversized tissue passageway. The GORE tunneler is comprised of a hollow rigid metal shaft connected to a handle with a removable bullet tip at one end of the shaft. The shaft is fabricated from stainless steel and fits into a formed handle with a center rod. The instrument is used to bluntly dissect a tunnel by forcing the bullet tipped hollow shaft through the tissue. After suture attachment of the graft material to the inner rod the vascular graft is then easily drawn through the entire length of the oversized hollow tube.

With the graft positioned in place, but still within the hollow shaft, the outer shaft tunneler must next be carefully extracted from the tissue tunnel without extracting the graft from the subcutaneous passageway. All rigid sheath tunneler devices may at times be difficult to extract from the tissue due to the compressive tension on the surrounding tissue and surface friction thereby created. The surgeon may find it necessary to use both hands to grasp the rigid hollow sheath, requiring an assistant to hold the vascular graft in position, hence, use of these type of instruments still may require significant surgical glove contact of the vascular graft during tunneling.

Another example of a two part rigid sheath tunneler is the "SCANLAN" tunneler, which is similar in operative technique to the GORE device except that the rigid sheath is constructed of hard plastic and considered disposable (1 time use). The hollow shaft or tube is produced from a thicker walled, rigid plastic tube material in contrast to the thin walled stainless steel tube used with the GORE device. The SCANLAN plastic hollow shaft includes a pressure fitted, removable bullet tip and an internal retractable rod. The surgeon forcibly passes the bullet shaped shaft tunneler through the tissue to create the tunnel. The bullet shaped tip of the plastic shaft is then removed and the vascular graft is attached to the inner rod with an alligator tip clamp located on the end of the pull-thru rod. Like the GORE tunneler, the SCANLAN tunneler allows the graft to be easily drawn into and through the oversized hollow shaft. With two hands, the rigid plastic tube is carefully withdrawn out of the patient over the graft thru the proximal exit wound or skin incision, leaving the vascular graft within the tissue tunnel. The graft is then detached from the rod. Similar to the metal sheath tunneler instruments, the rigid plastic tube may also at times be difficult to extract from the tissue tunnel due to the compressive tension created by the bluntly dissected tissue and the surface friction created along the indwelling rigid walled shaft.

As has been previously noted, tunnelers are expensive, and consequently hospitals maintain only a limited supply of these surgical devices for hospital use. Most instruments are reusable, and are required to be washed and sterilized between use. It sometimes happens that in an emergency situation whereby disposable devices are employed, the proper sized disposable shaft component is not available. Therefore, surgeons are at times forced to use improper sized tunneling devices or alternative subcutaneous dissection items such as a gloved finger, or hemostat clamp, or a sharp surgical instrument such as a thoracic catheter trocar stylette. Thus, the resulting tunnel created by these alternative sized devices may create too large a tunnel for the vascular graft and/or unnecessary bleeding and trauma, placing the vascular implant and patient at risk.

It is thus desirable to provide an implantable vascular graft that can be implanted with less surgical manipulation and less tissue trauma than with a traditional rigid sheath tunneler. More specifically, it would be desirable to insure a tunnel diameter matched to the same outside diameter of the vascular graft while protecting the implant from contamination and prewetting with blood in an easy to handle and removable sheath.

It is also an object of the invention to provide an implantable, vascular graft that includes a preattached tunneling tip for attachment to a tunneler instrument that substantially eliminates any plowing of the tissue when he graft is pulled through the tunnel track. Providing a preattached tunneler tip allows a quicker response by the surgeon during the implantation.

It is therefore desirable to provide for a tunneling device that allows for safe and easy implantation of a vascular graft device within a subcutaneous cavity while shielding the implanted graft during handling and manipulation by the surgeon. Contact exposure to the gloved hands of the surgeon or medical instruments that have come in contact with entry/exit skin wound, is thus minimized so as to reduce the potential for staphylococcal infection following implantation.

It is also desirable to provide for a tunneling device that incorporates a thin compressible sheath to protect an enclosed medical device without substantially increasing the outside diameter of the tunneling device. The thin compressible sheath is constructed of a smooth, flexible and easily compressive material for easy insertion within a tissue tunnel. A hydrophilic coating may also be applied to the sheath to increase its lubricousness to minimize tissue drag and tissue trauma during insertion of the implant or sheath removal after implant positioning.

It is further desirable to provide for a tunneling device implemented as an implantable, vascular graft that can be utilized with a conventional tunneler such as either the sheathless KELLY-WICK variety or rigid sheath GORE type tunneler instruments. Configured as a preassembled device, it is also desirable that the tunneling device be easily inserted into the tissue and protect an enclosed graft from contamination during the implantation process.

It is also desirable to provide for a tunneling device implemented as an implantable, vascular graft that includes a precision matched sized tunneler tip that is preattached to the graft in a near seamless fashion to effectively contain the leading edge or end of the graft to as to eliminate any plowing of tissue when the graft is pulled through the tunnel cavity.

It is also desirable to avoid prewetting or presoaking the vascular graft material with blood fluid during graft insertion to reduce the risk of poor tissue healing caused from graft leakages and/or seroma formation through a blood saturated graft wall.

SUMMARY OF THE INVENTION

Broadly speaking, the present invention addresses the disadvantages of prior tunneling devices, and provides for an implantable tunneling device which is advantageously protected from skin surface contact during the implantation process. In one aspect of the invention a medical device is enclosed in a thin collapsible sheath that surrounds the graft during the surgical insertion procedure. The sheath isolates the medical device from contact with contaminated surroundings such as the surface skin wound, surgical gloves and surgical instrumentation. The sheath provides a flexible, compressible outer surface for implantable medical devices that allows for easier insertion of the implant device into the tissue cavity with less trauma, less friction, less blunt dissection and less drag during placement. Due to the smoothness and collapsible low profile of the preattached sheath, this novel tunneling device is faster and easier to use, in addition to being less traumatic to tissue. This preattached sheath device may be made more lubricious by the application of a wide variety of coatings.

In a further aspect of the invention, a tunneling device is realized as a vascular graft that is enclosed in a sheath for surrounding the graft during the implantation process. The sheath protects the graft from non-sterile contact during implantation, and from skin incision contact and possible bacterial contamination. The thin collapsible sheath allows for easier insertion of the graft through the tissue cavity due to the unrestricted and flexible nature of the compressible outer surface. The preattached sheath may be coated on the outside surface with a lubricious substance to provide a low coefficient of friction, allowing the sheath and graft to be easily pulled through tissue by a tunneler.

In another aspect of the invention, a preattached tunneler tip is connected to either one end or both ends of a vascular graft at the point of the lumen. The precision matched size tunneler tip has a universal screw thread assembly to fit most conventional tunnel rods. The preattached tunneler tip is advantageously connected to the graft so as not to increase the outside diameter of the graft or create a sharp junction between the tip, the graft and the tunneler rod. Consequently when the graft sheath tip assembly is attached to the indwelling tunneler rod, the entire graft sheath tip assembly can be atraumatically drawn through the original tissue tunnel. Since the preattached graft sheath tip is closely matched in size to the outer diameter of the graft, the device allows for a tighter, frictionless insertion technique with less tissue trauma, leaving little or no space around the vascular graft for blood fluid to collect after implantation. This novel vascular graft device and insertion technique results in a more anatomical fit between the subcutaneous tissue and implant.

It is contemplated that the implantable device need not be completely implanted within the patient to be considered within the scope of the present invention. Examples of medical devices which are contemplated to be within the scope of the invention include but are not limited to non-lumenally placed catheters, transcutaneous tubing, artificial skin, drug delivery tubing devices, other artificial organs, and peritoneal dialysis catheters placed within the peritoneal body cavity.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DETAILED DESCRIPTION OF THE ILLUSTRATED EMBODIMENT

Figure 1:
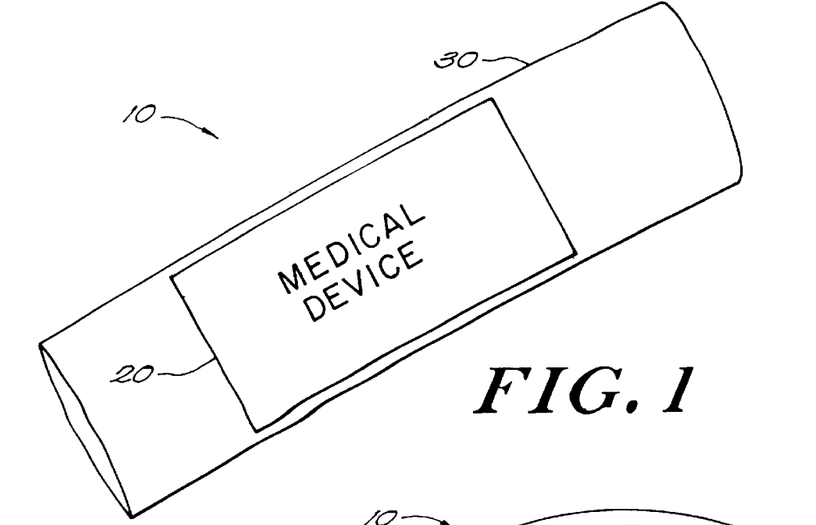
FIG. 1 is a depiction of a tunneling device comprised as a medical device enclosed by a sheath in accordance with the current invention.

FIG. 1 is a depiction of a tunneling device 10 that is comprised in the general case of a medical device 20, surrounded by a sheath 30. Tunneling device 10 is intended for implantation in the body of a patient to perform diagnostic or therapeutic functions. Medical device 20 may be realized as a heart pacemaker lead, a vascular graft, a penile implant, a catheter or similar implantable biological device. Further, medical device 20 may be a stent comprised of nitinol, stainless steel or other suitable metal optionally in combination with a biocompatible material. Sheath 30 is constructed of a flexible, compressive material that protects the medical device during implantation of the device into the tissue of a patient, and isolates medical device 20 from contamination during the process. Sheath 30 may be open at both ends or may be closed at one or both ends.

Sheath 30 is preferably fabricated from polyethylene. Sheath 30 is sized to have a inside diameter only slightly larger than the outside diameter of the device which it encompasses. The thickness of the cylindrical walls of sheath 30 is approximately 2 to 4 microns. One of ordinary skill in the art will recognize that although polyethylene is described as the preferred material for fabrication of sheath 30, other materials may be used that come within the scope of the invention. These materials include but are not limited to MYLAR ribbon, TEFLON ribbon, and polypropylene.

Figure 2:
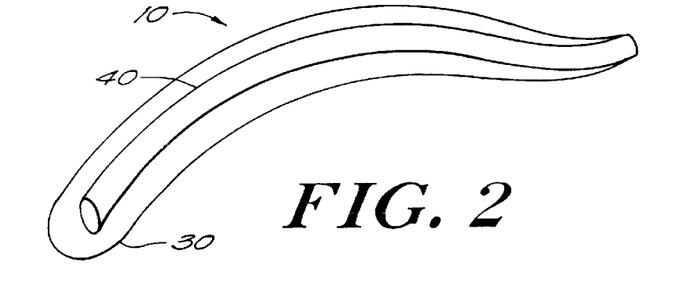
FIG. 2 is a depiction of a tunneling device realized as a vascular-graft enclosed by a sheath in accordance with the current invention.
Figure 3:
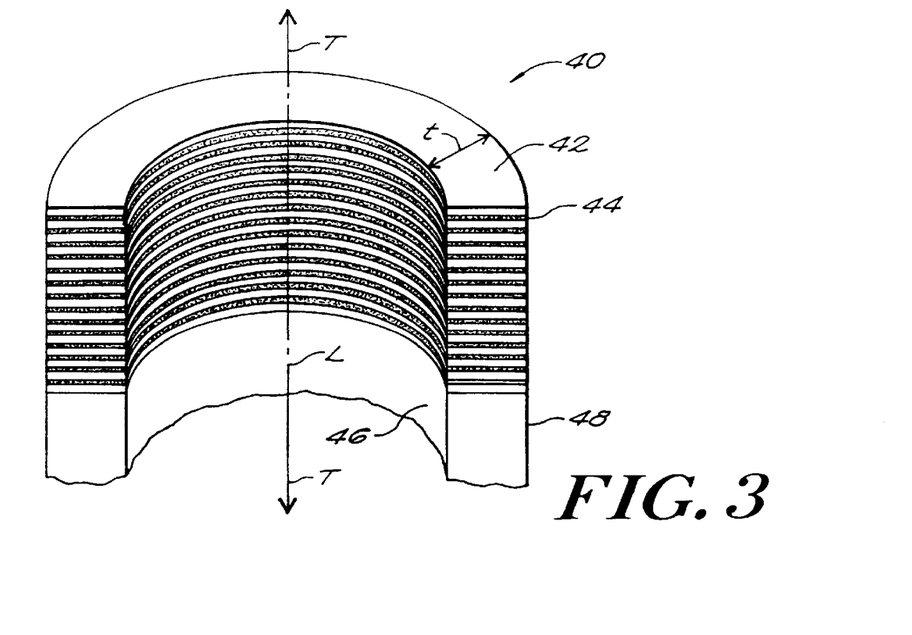
FIG. 3 is a depiction of a porous article suitable for construction of a vascular graft formed in accordance with the teachings of the present invention.

FIG. 2 shows a tunneling device 10 wherein medical device 20 is realized as a vascular graft 40 enclosed by a sheath 30 that advantageously protects graft 40 during the implantation of the graft. FIG. 3 is a cross-section depiction of vascular graft 40 in accordance with the current invention. One of ordinary skill in the art will recognize that the current invention is not directed to a specific vascular graft design, but is generically applicable to many different types of vascular grafts which may be constructed from different materials.

Examples of different vascular grafts that are contemplated to be within the scope of this invention include the grafts described in the following commonly assigned U.S. patent applications: U.S. Ser. No. 760,753 for "IMPLANTABLE PROSTHETIC DEVICE FOR THE DELIVERY OF A BIOACTIVE MATERIAL"; U.S. Ser. No. 760,716 for "MANUALLY SEPARABLE MULTI-LUMEN VASCULAR GRAFT"; U.S. Ser. No. 760,728 for "IMPLANTABLE PROSTHETIC DEVICE HAVING INTEGRAL PATENCY DIAGNOSTIC INDICIA"; U.S. Ser. No. 760,717 for "POLYLUMENAL IMPLANTABLE ORGAN"; and U.S. Ser. No. 760,718 for "SELF-SEALING IMPLANTABLE VASCULAR GRAFT" all of which were filed Sep. 16, 1991. The specifications of these applications for patent are hereby incorporated herein by reference.

While acknowledging that many different types of vascular grafts are suitable to practice the invention, a vascular graft 40 formed by the methods described in U.S. Pat. No. 5,474,824 is preferred. This graft is manufactured by Atrium Medical Corporation, 5 Wentworth Drive, Hudson, N.H. 03051 and marketed as the ATRIUM HYBRID PTFE graft.

For purposes of disclosure, vascular graft 40 will be described in accordance with the preferred graft, but this description is not to be construed as limiting. In the drawings, the microstructure of vascular graft 40 has been exaggerated. Accordingly, while the dimensions of the microstructure are enlarged, the general character of the illustrated microstructure is representative of that microstructure prevailing in vascular graft 40.

Vascular graft 40 is preferably constructed from porous polytetrafluoroethylene (PTFE) material, but may also be fabricated from polyester or polyurethane material. The vascular graft 40 includes a microstructure characterized by elongate nodes 42 interconnected by fibrils 44. A significant feature of the vascular graft 40 is that the nodes 42 are ring-shaped to form, in effect, a series of washer-type, or plate-like solid bodies circumscribing the vascular graft's longitudinal axis L. The nodes 42 are oriented generally radially, i.e., perpendicularly to the axis of stretching, represented by arrows T which is coincident with the longitudinal axis L.

Another significant feature of the vascular graft's microstructure is that substantially all of the nodes 42 extend along a transverse axis from an inner surface 16 of the vascular graft to an outer surface 48 of the vascular graft. This dimension of the nodes 12 along the inside-to-outside direction is significantly larger than the corresponding dimension of nodes formed by conventional single-resin fluoropolymer processing methods. Such nodes are randomly arranged and may be characterized by a transverse axis which is generally oriented perpendicularly to the axis of stretch. Notably, however, the nodes of these known structures are considerably shorter and smaller than nodes produced in accordance with the present invention. Nodes formed by this conventional technique generally range in size from smaller than one micron to approximately 400 microns.

Vascular graft 40 provides a microporous structure having microfibrillar spaces which define through-pores or channels extending entirely from the inner to the outer wall of the expanded extrudate. These through-pores are perpendicularly oriented internodal spaces which traverse from one surface to another.

By varying lubricant levels internodal through-pores are preferentially altered such that the surface pore on one surface is made to be larger or smaller than the surface pore on the opposing surface.

Figure 4:
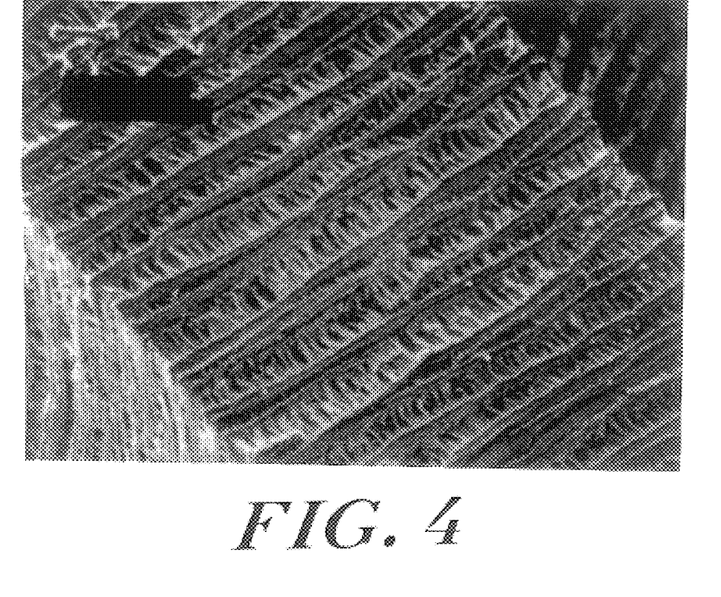
FIG. 4 is a scanning electron microscopic view of a longitudinal crosssection of a porous article in accordance with the invention.

A longitudinal cross-section view of a preferred vascular graft according to the current invention is shown in FIG. 4. The vascular graft is an article having a microstructure characterized by elongate nodes which are substantially larger than the nodes of materials produced by known single-resin forming methods. Indeed, the nodes shown in FIG. 3 consistently range in size from approximately 500 microns to approximately 900 microns. Substantially all of the nodes of the article shown in FIG. 3 extend from the inner surface of the tubular article to the outer surface of the tubular article, thereby creating throughpores substantially all of which traverse from one surface of the article to the other.

Figure 5:
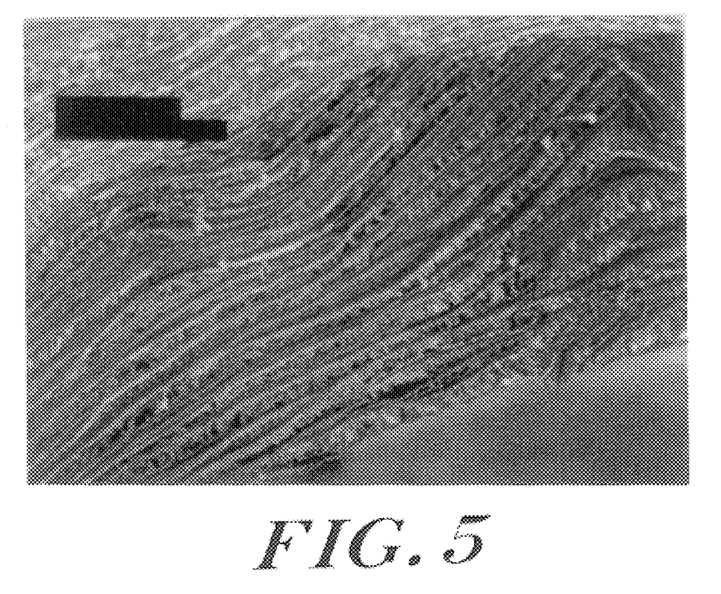
FIG. 5 is a scanning electron microscopic view of a radial cross-section of a porous article in accordance with the invention.

FIG. 5 is a radial cross-section view of the vascular graft shown in FIG. 4. There it can be seen that while the nodes are generally oriented perpendicularly to the axis of stretch, as represented in FIG. 3, they are not perfectly flat and, therefore, a radial cross-section cuts through many nodes. Accordingly, while the schematic depiction in FIG. 3 is useful for purposes of explanation, the scanning electron microscope photographs in FIGS. 4 and 5 are more accurate depictions of the microstructure of a product.

Several structural, clinical and biological advantages accrue from the microstructure of the preferred vascular graft 40. Larger node size provides a structure having a significantly improved radial tensile strength. Also, the preferred vascular graft 40 has improved burst pressure and suture strength characteristics. The flat ring-like node structure imparts significantly more flexibility, without kinking, than conventional fluoropolymer processes, in addition to providing superior resistance to radial twist compression (colloquially known as "torque twist"). The vascular graft allows a significant degree of bending or radial twist, before experiencing lumen collapse or kinking, unlike typical fluoropolymer articles which exhibit significantly less resistance to "torque twist" or "bending."

The preferred vascular graft 40 of the current invention exhibits significantly more resistance to compression than conventionally processed articles. This provides more resistance to luminal collapse under equivalent stress loads. The graft also exhibits increased flexibility for enhanced drapability, or ability to bend more readily, without restricting luminal cross-sectional area, thereby improving ease of handling during surgery, while not increasing stress on the points of attachment and fixation. The ring like nodal architecture of the preferred vascular graft also produces tubular structures with significantly more resistance to tearing or splitting in the horizontal direction, as compared to conventional non-reinforced fluoropolymer tubular articles.

Referring again to FIG. 2, sheath 30 is a low-profile cylindrical tube made of a flexible and compressive material that encloses vascular graft 40 along the longitudinal axis of the graft 40 to protect the graft 40 during the implantation process. Sheath 30 is preferably fabricated from polyethylene, and may be open at both ends or closed at one or both of the ends. Sheath 30 is preferably translucent in order to allow observation of registration markings on the graft 40 to assure the physician that the graft 40 is not kinked during implantation. Graft 40 is sized to have a inside diameter only slightly larger than the outside diameter of the graft which it encompasses. The thickness of the cylindrical walls of sheath 30 is approximately 2 to 4 microns. One of ordinary skill in the art will recognize that although polyethylene is described as the preferred material for fabrication of sheath 30, other materials may be used that come within the scope of the invention. These materials include but are not limited to MYLAR ribbon, TEFLON ribbon, and polypropylene.

Tunneling device 10, represented as graft 40 having an enclosing sheath 30, is designed for insertion within a tunnel cavity, and thus it is advantageous for the tunneling device to have a low coefficient of friction for ease of insertion and subsequent removal of the sheath after implantation of the graft. Sheath 30 is preferably fixedly attached to vascular graft 40 at one end of the graft, but it is clear to one of ordinary skill in the art that sheath 30 may be provided separately, as shown in FIG. 1, and attached to vascular graft 40 by the surgeon during the grafting process. Sheath 30 may be joined to the vascular graft 40 using simple mechanical means or a compression fit collar or stapled or sutured or other fastening techniques acceptable for implantation within the tissue of the body. Sheath 30 is preferably fabricated from polyethylene. Polyethylene is a soft and ductile material that accommodates the flexibility of vascular graft 40, and when rented or compacted, the coefficient of friction is not appreciatively increased. In one embodiment of the invention, sheath 30 may be coated with a lubricous material to further decrease its coefficient of friction. Sheath 30 may also be coated with hydrophilic materials to facilitate insertion of the device or chemotherapeutic agents for delivery of therapeutic materials.

Figure 6:
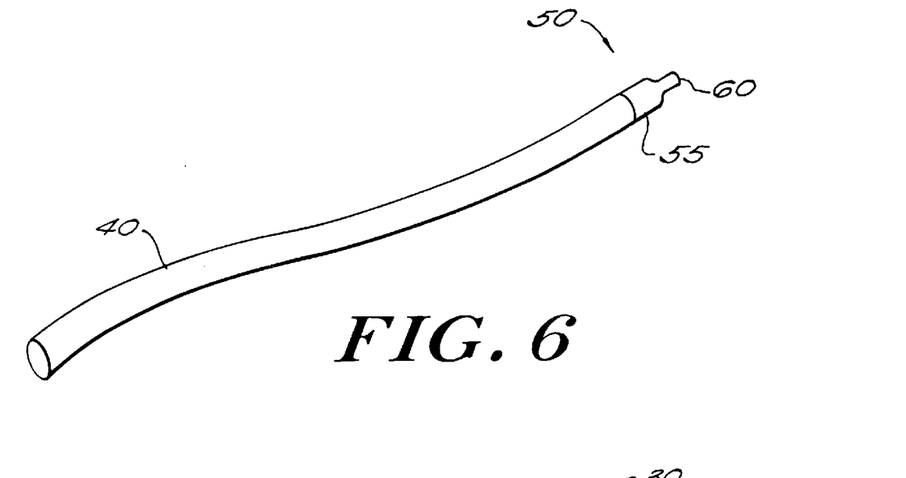
FIG. 6 is a depiction of a tunneling device realized as a vascular graft and having a tunneler tip coupled at one lumen of the device.
Figure 7:
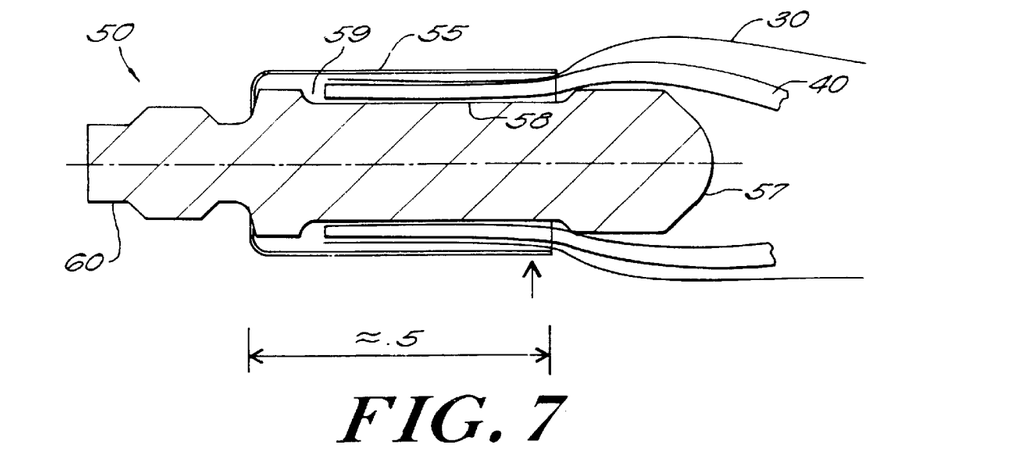
FIG. 7 is a depiction of a tunneling device realized as a vascular graft with a protective sheath and having a tunneler tip coupled at one lumen of the device in accordance with one embodiment of the invention.
Figure 8:
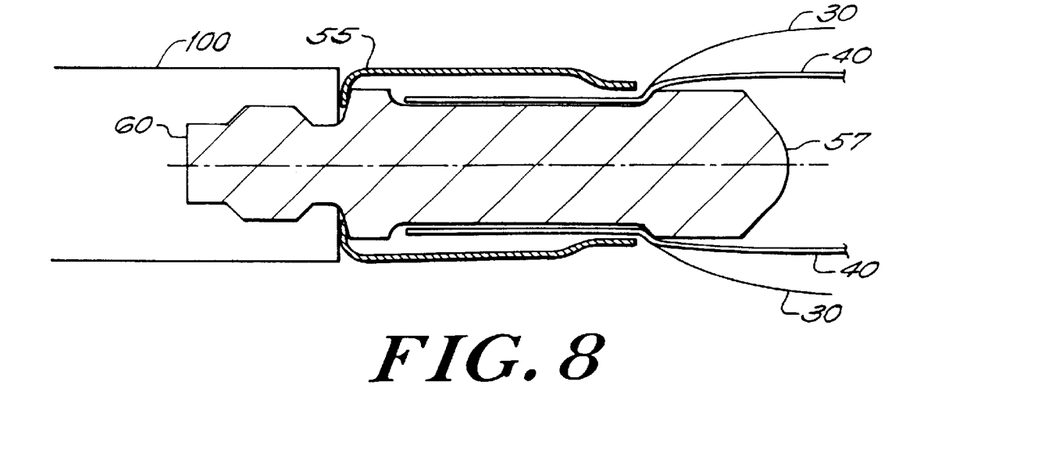
FIG. 8 is a depiction of the tunneling device of FIG. 7, showing a swaged tunneler tip.

FIG. 6 shows a further embodiment in accordance with the current invention that includes a vascular graft 40 for implantation. A tunneler tip 50 is connected to one end of the graft to attach the graft 40 to a tunneler instrument for urging the graft through the tissue. In one practice of the invention, tunneler tip 50 includes a cylindrical ferrule 55 that encloses the outer surface of vascular graft 40 at one end of the graft. Referring now to FIG. 7, ferrule 55 houses a solid core 57 that is generally cylindrical in shape. Core 57 includes a beveled groove 58 around the periphery of core 57 to define an annular channel 59 between core 57 and ferrule 55. Channel 59 defines an annular opening sufficient to accept graft 40 and sheath in the beveled groove 58 between ferrule 55 and core 57. Tunneler tip 50 is coupled to the graft 40 by crimping the ferrule 55 of the tip 50 to core 57, enclosing graft 40 and sheath 30 within channel 59, thus fixedly positioning graft 40 and sheath 30 therein. Tunneling device 10 may be prepackaged with vascular graft 40 and sheath 30 crimped within ferrule 55 or delivered with vascular graft 40 and sheath 30 enclosed within channel 59, but requiring crimping by a physician for a permanent attachment. As shown in FIG. 8, tunneler tip 50 is swaged at the end of ferrule 55 in a recessed fashion to create a substantially seamless connection that does not appreciatively increase the outside diameter of the graft 40 to prevent plowing of the tissue and further dissection when the graft is pulled through a tunneled passageway. In an alternative practice of the invention graft 40 includes internal threads on the inside surface of the vascular graft 40 for screwing tunneler tip 50 into the lumen of the graft. In a yet further embodiment, vascular graft 40 and or sheath 30 may be inserted into channel 59, and remain fixedly attached to the graft as a result of frictional contact of the ferrule 55 and core 57 without crimping. Other methods for attaching the tunneler tip 50 to the graft are considered to be within the scope of the invention that do not appreciatively increase the outside diameter of the graft 40. It is intended that the attachment does not create a substantial lip that allows plowing of the tissue when the graft is pulled through the tunnel cavity. It is dimensionally sized to avoid plowing of the tissue. Tunneler tip 50 is preferably constructed of stainless steel, but one of ordinary skill in the art will recognize that other materials may be suitable to connect the graft 40 to the tunneling device. One such example of an alternative material is a hard plastic.

Figure 10:
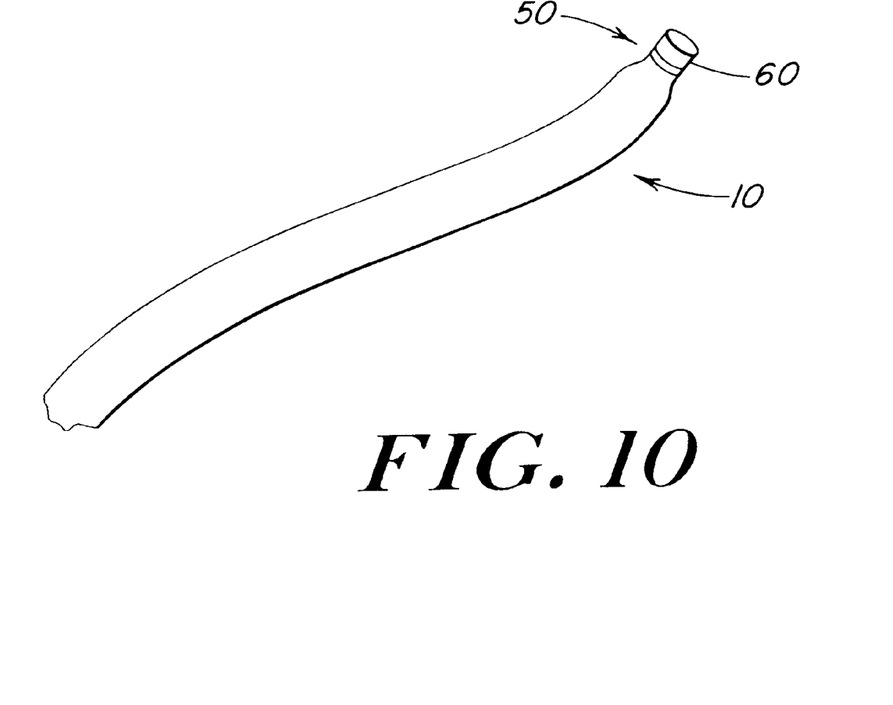
FIG. 10 is a depiction of the tunneling device in accordance with the invention having a male screw for a connector.
Figure 11:
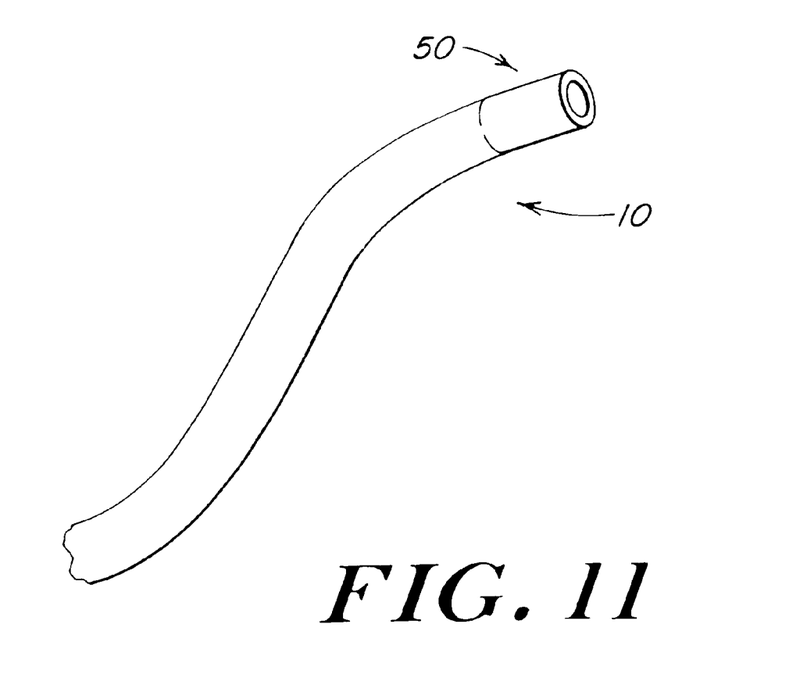
FIG. 11 is a depiction of the tunneling device in accordance with the invention having a snap-on fit for a connector.

Tunneler tip 50 includes a connector 60 for attachment of the tunneler tip to a tunneler instrument. In one practice of the invention, connector 60 is a screw mechanism as shown in FIG. 10, using universal screw threads for connecting the tunneling tip 50 to the tunneler instrument. Other conventional methods of fastening the tunneler tip to the tunneling device including snap-on technique as shown in FIG. 11, that allow tunneler tip 50 to snap into a tunneling device, or clip on fasteners will be recognized by those of ordinary skill in the art as applicable to the practice of the invention, and are contemplated to be within the scope of the invention.

Figure 12:
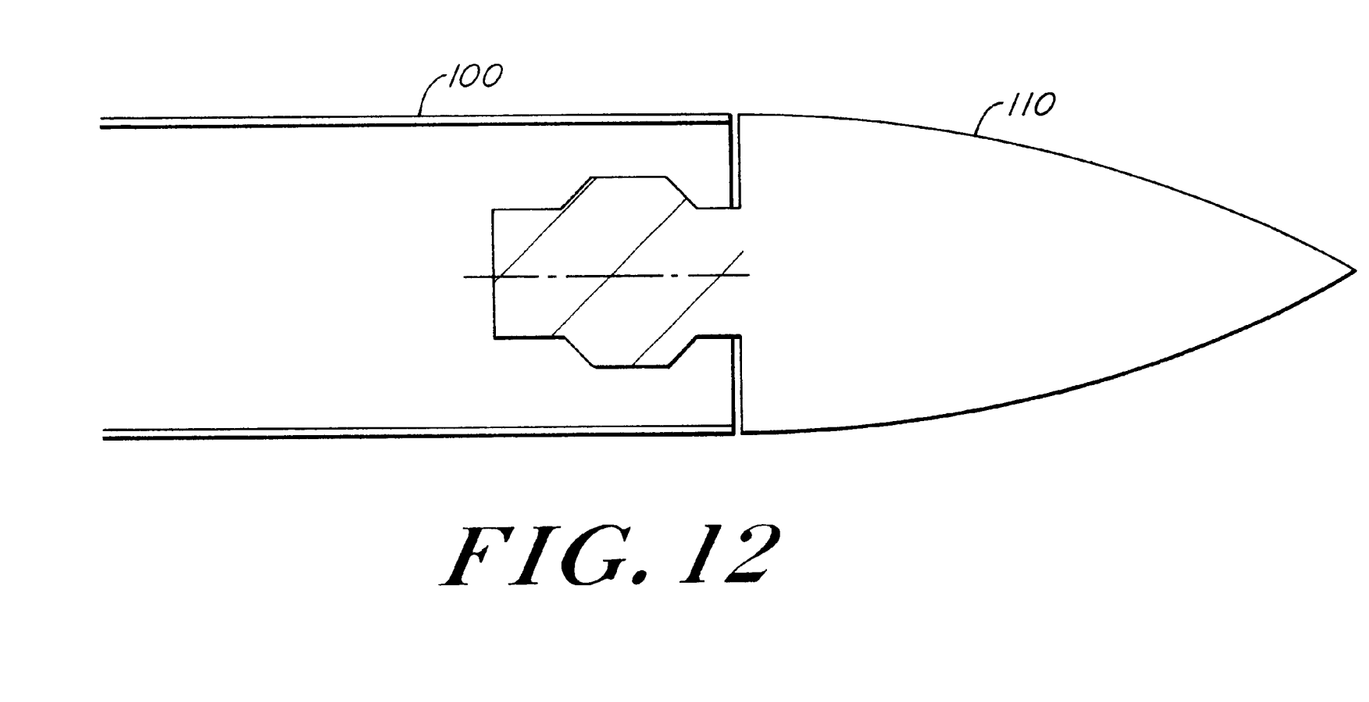
FIG. 12 is a depiction of a tip portion attached to a tunneling device.

FIG. 12 illustrates an example of a tip portion of 110 connected to the tunneling instrument 100. As illustrated by FIGS. 8 and 12, the tip portion 110 and connector 60 are interchangeably mountable to the tunneling instrument 100.

Figure 9:
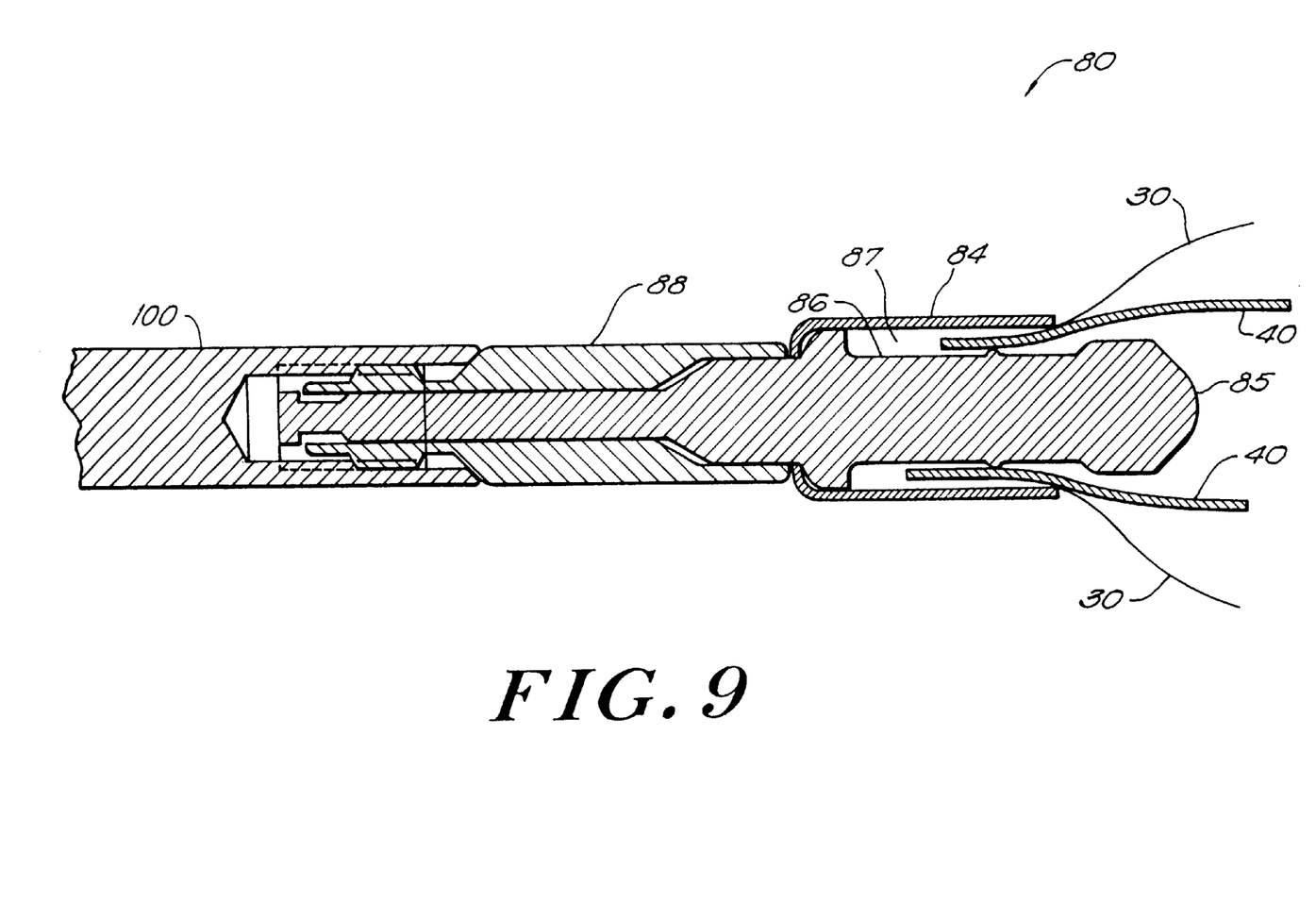
FIG. 9 is a depiction of the tunneling device in accordance with the invention having a swivel tunneler tip.

In another embodiment as shown in FIG. 9, tunneler tip 80 has a swivel mechanism that allows connector 82 to be screwed into the tunneler instrument without rotating the graft and changing the orientation of the tunneling device with the tunneler instrument. In this embodiment, tunneler tip 80 includes a ferrule 84 that houses a solid core 85 which is generally cylindrical in shape. Core 85 includes a beveled groove 86 around the periphery of core 85 to define an annular channel 87 between core 85 and ferrule 84. Core 85 is coupled to a swivel rod 88 having connector 82 at its distal end for connecting to a tunneler instrument Swivel rod 88 is coupled to core 85 so that swivel rod 88 is rotatable about its longitudinal axis allowing the device to be connected with rotating the graft 40. Channel 87 defines an annular opening sufficient to accept graft 40 and sheath in the beveled groove 86 between ferrule 84 and core 85. Tunneler tip 80 is coupled to the graft 40 by crimping the ferrule 84 of the tip 80 to core 85, enclosing graft 40 and sheath 30 within beveled groove 86, and fixedly positioning graft 40 and sheath 30 therein.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed as new and desired to be secured by letters patent is:

1. A system for subcutaneously deploying a graft in a patient, the system comprising:
    a tunneling instrument for use in a subcutaneous tissue cavity in the patient,
    a connector coupled to said tunneling instrument for connecting the graft to said tunneling instrument, said graft mounted to said connector, and
    a flexible, thin film sheath attached to and enclosing at least one end and a portion of the length of the graft to protect the graft from contamination during implantation of the graft into the subcutaneous tissue cavity formed in the patient.

2. The system of claim 1, wherein said sheath is composed of at least one of the group consisting of polytetrafluoroethylene, polyethylene, TEFLON, MYLAR, and polypropylene.

3. The system of claim 1, wherein said sheath encloses both ends of the graft.

4. The system of claim 1, wherein said connector for connecting the graft to said tunneling instrument provides a sutureless connection of the graft to said tunneling instrument.

5. The system of claim 4, wherein said connector includes a screw thread formed on a surface thereof to provide said sutureless connection of the graft to said tunneling instrument.

6. The system of claim 4, wherein a portion of said connector is sized and shaped to provide a snap-fit connection with said tunneling instrument.

7. The system of claim 4, wherein said tunneling instrument comprises a shaft and a tip portion removably attached to an end of said shaft, said connector connecting the graft to said shaft of said tunneling instrument upon removal of the tip portion.

8. The system of claim 7, wherein said connector has a diameter approximately no greater than the diameter of said shaft of said tunneling instrument.

9. The system of claim 4, wherein said connector comprises
    a core having a groove formed around a periphery thereof, and
    a cylindrical ferrule positioned about said groove, a portion of said sheath and the graft being positioned between said ferrule and said core within said groove, said ferrule being crimped about said core to fix said sheath and the graft to said connector.

10. The system of claim 9, wherein said connector includes a swivel rod connected at one end to said core and at another end to the tunneling instrument, the swivel rod being rotatable about a longitudinal axis of said swivel rod to facilitate attachment of the graft to said tunneling instrument.

11. The system of claim 4, wherein said connector is configured to rotate relative to the tunneling instrument to facilitate attachment of the graft to said tunneling instrument.

12. The system of claim 4, wherein said tunneling instrument comprises a shaft having an end and adapted to interchangeably mount a tip portion and said connector to said end.

13. The system of claim 1, wherein said sheath is coated with at least one of the group consisting of a lubricous material, a hydrophilic material, and a chemotherapeutic agent.

14. A system for subcutaneously deploying a graft in a patient, the system comprising:

a tunneling instrument for use in a subcutaneous tissue cavity in the patient, the tunneling instrument comprising a shaft and a tip removably attached to said shaft, a connector providing a sutureless connection of the graft to said tunneling instrument, said connector attaching the graft to said shaft of said tunneling instrument upon removal of said tip from said shaft, and a flexible, thin film sheath attached to said graft, said sheath enclosing one end of the graft, said sheath extending along and enclosing a portion of the length of the graft to protect the graft from contamination during implantation of the graft into the subcutaneous tissue cavity formed in the patient.

15. A system for subcutaneously deploying a graft in a patient, the system comprising:

a tunneling instrument for use in a subcutaneous tissue cavity in the patient, the tunneling instrument comprising a shaft and a removable bullet tip at an end of said shaft, a connector providing a sutureless connection of the graft to said tunneling instrument, said connector attaching the graft to said end of said shaft upon removal of said tip, and a flexible, thin film sheath attached to said graft, said sheath enclosing one end of the graft, said sheath extending along and enclosing a portion of the length of the graft to protect the graft from contamination during implantation of the graft into the subcutaneous tissue cavity formed in the patient.

* * * * *